(12) United States Patent
Belko et al.

(10) Patent No.: US 6,303,798 B1
(45) Date of Patent: Oct. 16, 2001

(54) METHYLENE DIOXY TETRAHYDROINDANE DERIVATIVE

(75) Inventors: Robert P. Belko, Monroe; Mark A. Sprecker, Sea Bright; Charles E. J. Beck, Summit, all of NJ (US)

(73) Assignee: International Flavors & Fragrances Inc., New York, NY (US)

( * ) Notice: Subject to any disclaimer, the term of this patent is extended or adjusted under 35 U.S.C. 154(b) by 0 days.

(21) Appl. No.: 09/791,296

(22) Filed: Feb. 23, 2001

(51) Int. Cl.[7] .......................... C07D 319/08; C11D 3/50; A61K 7/46
(52) U.S. Cl. .......................... 549/359; 510/104; 512/13
(58) Field of Search .............................. 424/401; 512/13; 510/104; 549/359

(56) References Cited

U.S. PATENT DOCUMENTS

| | | | |
|---|---|---|---|
| 3,422,155 | 1/1969 | Dowbenko | 570/187 |
| 3,511,796 | 5/1970 | Wright | 521/146 |
| 3,636,165 | 1/1972 | Hall | 568/819 |
| 3,647,826 | 3/1972 | Hall | 549/545 |
| 3,681,464 * | 8/1972 | Theimer | 568/374 |
| 3,806,472 | 4/1974 | Hall | 512/14 |
| 3,927,083 * | 12/1975 | Hall et al. | 512/13 |
| 4,534,891 | 8/1985 | Boden et al. | 510/101 |
| 4,634,548 * | 1/1987 | Helmlinger et al. | 426/536 |
| 4,902,840 | 2/1990 | Sprecker et al. | 570/187 |
| 4,933,319 * | 6/1990 | Sprecker et al. | 512/13 |
| 5,002,929 * | 3/1991 | Bruns et al. | 512/18 |
| 5,665,698 * | 9/1997 | Narula et al. | 512/19 |

* cited by examiner

*Primary Examiner*—Michael G. Hartley
*Assistant Examiner*—Michael A. Willis
(74) *Attorney, Agent, or Firm*—Joseph F. Leightner

(57) ABSTRACT

The present invention is directed to a novel dioxin compound and the use of the novel compound in creating fragrances, and scents in items such as perfumes, colognes and personal care products.

7 Claims, No Drawings

METHYLENE DIOXY TETRAHYDROINDANE DERIVATIVE

FIELD OF THE INVENTION

The present invention relates to new chemical entities and the incorporation and use of the new chemical entities as fragrance chemicals.

BACKGROUND OF THE INVENTION

U.S. Pat. No. 4,902,840, hereby incorporated by reference, discloses the use of substituted tetrahydroindane derivatives as useful fragrance chemicals. Despite this disclosure and numerous other patents on fragrance materials, there is a continuing need to provide additional fragrance materials such that perfumers may create new fragrances for various applications.

SUMMARY OF THE INVENTION

The present invention provides a novel chemical, and the use of this chemical to enhance the fragrance of perfumes, toilet waters, colognes, personal products and the like. In addition, the present invention is directed to the use of the novel chemical to enhance fragrance in perfumes, toilet waters, colognes, personal products and the like.

More specifically, the present invention is directed to the novel compound, 4,4a,5,6,7,8,9,9b octahydro-7,7,8,9,9-pentamethyl-indano[4,5-d]-dioxin, which is understood to be represented by the formula below:

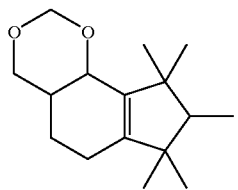

Another embodiment of the invention is a method for enhancing a perfume by incorporating an olfactory acceptable amount of the compound provided above.

These and other embodiments of the present invention will be apparent by reading the following specification.

DETAILED DESCRIPTION OF THE INVENTION

The novel compound of the present invention is prepared by the reaction of 6,7-dihydro-1,2,3,4,5-pentamethyl indane, which is disclosed and claimed in U.S. Pat. No. 4,902,840, with formaldehyde. Preferably the formaldehyde is diluted, having a value of from about 20 to about 50, preferably 30 to about 40 and most preferably about 37 weight percent. An acid catalyst is preferably employed in the reaction. The acid is preferably a mineral acid, such as sulfuric acid or hydrochloric acid, most preferably provided in a concentrated form. A preferred method of carrying out the reaction is by refluxing the components at an elevated temperature, from about 50 to about 120° C., preferably from about 65 to about 110° C. and most preferably at about 105° C.

The compound of the present invention has a powerful musk fragrance, with sweet, powdery, spicy and nitromusk notes.

The use of the compound of the present invention is widely applicable in current perfumery products, including the preparation of perfumes and colognes, the perfuming of personal care products such as soaps, shower gels, and hair care products as well as air fresheners and cosmetic preparations. The present invention can also be used to perfume cleaning agents, such as, but not limited to detergents, dishwashing materials, scrubbing compositions, window cleaners and the like.

In these preparations, the compounds of the present invention can be used alone or in combination with other perfuming compositions, solvents, adjuvants and the like. The nature and variety of the other ingredients that can also be employed are known to those with skill in the art.

Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk, flower scents such as lavender-like, rose-like, iris-like, carnation-like. Other pleasant scents include herbal and woodland scents derived from pine, spruce and other forest smells. Fragrances may also be derived from various oils, such as essential oils, or from plant materials such as peppermint, spearmint and the like.

A list of suitable fragrances is provided in U.S. Pat. No. 4,534,891, the contents of which are incorporated by reference as if set forth in its entirety. Another source of suitable fragrances is found in *Perfumes, Cosmetics and Soaps,* Second Edition, edited by W. A. Poucher, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

Olfactory effective amount is understood to mean the amount of compound in perfume compositions the individual component will contribute to its particular olfactory characteristics, but the olfactory effect of the perfume composition will be the sum of the effects of each of the perfumes or fragrance ingredients. Thus the compounds of the invention can be used to alter the aroma characteristics of the perfume composition, or by modifying the olfactory reaction contributed by another ingredient in the composition. The amount will vary depending on many factors including other ingredients, their relative amounts and the effect that is desired.

The level of compound of the invention employed in the perfumed article varies from about 0.005 to about 10 weight percent, preferably from about 0.5 to about 8 and most preferably from about 1 to about 7 weight percent. In addition to the compounds other agents can be used in conjunction with the fragrance. Well known materials such as surfactants, emulsifiers, polymers to encapsulate the fragrance can also be employed without departing from the scope of the present invention.

Another method of reporting the level of the compounds of the invention in the perfumed composition, i.e., the compounds as a weight percentage of the materials added to impart the desired fragrance. The compounds of the invention can range widely from 0.005 to about 70 weight percent of the perfumed composition, preferably from about 0.1 to about 50 and most preferably from about 0.2 to about 25 weight percent. Those with skill in the art will be able to employ the desired level of the compounds of the invention to provide the desired fragrance and intensity.

The following are provided as specific embodiments of the present invention. Other modifications of this invention will be readily apparent to those skilled in the art. Such modifications are understood to be within the scope of this invention. As used herein all percentages are weight percent unless otherwise noted, ppm is understood to stand for parts per million and g is understood to be grams. IFF as used in the examples is understood to mean International Flavors & Fragrances Inc.

EXAMPLE 1

Preparation of 4,4a5,6,7,8,9,9b-octahydro-7,7,8,9,9-pentamethyl-indano[4,5-d]-dioxin A mixture of 700 grams of 37 weight % formaldehyde, 60 grams of concentrated sulfuric acid and 600 grams of a solution of 40 weight percent 6,7-dihydro-1,1,2,3,3-pentamethylindane, 10 weight percent hexahydro-1,1,2,3,3-pentamethylindane and 40 weight percent 1,1,2,3,3,-pentamethylindane was heated at reflux at 108° C. for four hours. The mixture was then cooled to 50° C. Toluene (400 grams) and 10% HCl (500 milliliters) was added to the mixture. The aqueous layer was discarded and the organic layer was washed twice with 500 milliliters of 10% sodium carbonate solution.

The organic layer was distilled to recover the toluene, as well as 290 grams of a mixture of hexahydro-1,1,2,3,3,-pentamethylindane, 1,1,2,3,3-pentamethindene (boiling point 94–104° C. at 2 mm) and 179 grams 4,4a,5,6,7,8,9,9b octahydro-7,7,8,9,9-pentamethyl-indano [4,5-d]-dioxin (boiling point 120–125° C. at 3 mm).

The nmr spectrum of the 4,4a,5,6,7,8,9,9b-octahydro-7,7,8,9,9-pentamethylindano[4,5-d]-dioxin is as follows: 0.81–1.10 ppm (ms, 15H), 1.16–2.35 ppm (m, 5H), 3.81–4.08 ppm (m,3H), 4.62 ppm (m, 1H), 4.86 ppm (d, 1H).

EXAMPLE 2

Incorporation of 4,4a5,6,7,8,9,9b-octahydro-7,7,8,9,9-pentamethyl-indano[4,5-d]-dioxin into a fragrance formulation.

A fragrance was prepared according to the following formulation:

| Material | Parts |
| --- | --- |
| TRIPLAL ® (IFF) | 0.8 |
| Allyl cyclohexyl propionate | 0.5 |
| BORNAFIX ® (IFF) | 10.4 |
| CYCLABUTE ® (IFF) | 9.0 |
| APHERMATE ® (IFF) | 15 |
| Ethyl methyl phenyl glycidate | 1.0 |
| CYCLOGALBANIFF (IFF) | 0.5 |
| Isoamylbutyrate | 1.0 |
| ISOCYCLOCITRAL ® (IFF) | 0.5 |
| JASMAL ® (IFF) | 3.0 |
| Menthone | 0.3 |
| Peach aldehyde | 12.0 |
| 4,4a,5,6,7,8,9,9b-octahydro-7,7,8,9,9-pentamethyl-indano[4,5-d]-dioxin | 10.0 |
| Phenyl acetate | 4.0 |
| HC VERDOX ® (IFF) | 28 |
| FRUCTONE ® (IFF) | 4.0 |

The fragrance was described as having a green, musky scent from the incorporation of the compound of the present invention.

What is claimed is:

1. The compound 4,4a,5,6,7,8,9,9b-octahydro-7,7,8,9,9-pentamethyl-indano[4,5-]-dioxin.

2. The process to produce the compound of claim 1, wherein 6,7-dihydro-1,2,3,4,5-pentamethylindane is reacted with aqueous formaldehyde in the presence of a mineral acid catalyst at temperatures ranging from 65 to 110° C.

3. A fragrance comprising the compound of claim 1.

4. A method for improving, enhancing or modifying the odor properties of a fragrance by incorporating an olfactory acceptable amount of 4,4a,5,6,7,8,9,9b-octahydro-7,7,8,9,9-pentamethyl-indano-[4,5-d]-dioxin.

5. The method of claim 4 wherein the fragrance is incorporated into a product selected from perfumes, colognes, toilet waters, personal care products, cleaning products and air fresheners.

6. The method of claim 5 wherein the cleaning product is selected from the group consisting of detergents, dishwashing compositions, scrubbing compounds and window cleaners.

7. The method of claim 5 wherein the product is a personal care product.

* * * * *